(12) United States Patent
Chen et al.

(10) Patent No.: US 10,327,770 B2
(45) Date of Patent: Jun. 25, 2019

(54) LINEAR CUTTING STAPLER

(71) Applicant: Suzhou Touchstone International Medical Science Co., Ltd., Suzhou (CN)

(72) Inventors: Wangdong Chen, Suzhou (CN); Tuo Shu, Suzhou (CN); Kaifen Fu, Suzhou (CN); Sumei Zhang, Suzhou (CN)

(73) Assignee: Suzhou Touchstone International Medical Science Co., Ltd., Suzhou (CN)

( * ) Notice: Subject to any disclaimer, the term of this patent is extended or adjusted under 35 U.S.C. 154(b) by 439 days.

(21) Appl. No.: 15/104,667

(22) PCT Filed: Dec. 12, 2014

(86) PCT No.: PCT/CN2014/093677
§ 371 (c)(1),
(2) Date: Jun. 15, 2016

(87) PCT Pub. No.: WO2015/090157
PCT Pub. Date: Jun. 25, 2015

(65) Prior Publication Data
US 2017/0000484 A1    Jan. 5, 2017

(30) Foreign Application Priority Data

Dec. 17, 2013 (CN) .......................... 2013 1 0691699
Dec. 17, 2013 (CN) ...................... 2013 2 0831894 U

(51) Int. Cl.
*A61B 17/072* (2006.01)
*A61B 17/068* (2006.01)
(Continued)

(52) U.S. Cl.
CPC ...... *A61B 17/07207* (2013.01); *A61B 17/068* (2013.01); *A61B 17/072* (2013.01);
(Continued)

(58) Field of Classification Search
CPC ............... A61B 17/068; A61B 17/072; A61B 17/07207; A61B 17/115;
(Continued)

(56) References Cited

U.S. PATENT DOCUMENTS 3,490,675 A * 1/1970 Green .............. A61B 17/07207
227/19
3,499,591 A * 3/1970 Green .............. A61B 17/07207
227/19
(Continued)

FOREIGN PATENT DOCUMENTS

CN          2759400 Y     2/2006
CN        101869497 A    10/2010
(Continued)

OTHER PUBLICATIONS

European Search Report dated Jul. 11, 2017 for EP Application No. 14871911.5.

*Primary Examiner* — Scott A Smith
(74) *Attorney, Agent, or Firm* — Fox Rothschild LLP

(57) ABSTRACT

A linear cutting stapler comprising an upper jaw and a lower jaw capable of being closed or open relative to each other. The upper jaw includes an anvil and the lower jaw includes a staple cartridge frame. The proximal end of the anvil is provided with a positioning pin or a pin slot, and the proximal end of the staple cartridge frame is configured with a pin slot or a positioning pin. Wherein, the pin slot is engaged with said positioning pin, and the positioning pin comprises a first slot position and a second slot position relative to the pin slot. After the upper jaw and the lower jaw are open, the positioning pin is held in the second slot position, by this time the operator can lift up the whole stapler by holding upper jaw or lower jaw, which is convenient for re-locating the tissue and simplifies the operations.

17 Claims, 4 Drawing Sheets

(51) Int. Cl.
*A61B 17/10* (2006.01)
*A61B 17/29* (2006.01)
*A61B 17/00* (2006.01)
*A61B 17/115* (2006.01)

(52) U.S. Cl.
CPC ........... *A61B 17/105* (2013.01); *A61B 17/115* (2013.01); *A61B 2017/00367* (2013.01); *A61B 2017/07214* (2013.01); *A61B 2017/07257* (2013.01); *A61B 2017/07271* (2013.01); *A61B 2017/07285* (2013.01); *A61B 2017/2936* (2013.01)

(58) Field of Classification Search
CPC ........... A61B 2017/07214; A61B 2017/07271; A61B 2017/07285; A61B 2017/00367; A61B 2017/2936; A61B 2017/2945; A61B 2090/0814
USPC .............. 227/19, 175.2, 176.1, 180.1, 175.1; 606/139, 153, 219
See application file for complete search history.

(56) References Cited

U.S. PATENT DOCUMENTS

| | | | | |
|---|---|---|---|---|
| 4,429,695 A | * | 2/1984 | Green | A61B 17/07207 227/176.1 |
| 4,520,817 A | * | 6/1985 | Green | A61B 17/07207 206/339 |
| 4,863,088 A | | 9/1989 | Redmond et al. | |
| 5,129,570 A | * | 7/1992 | Schulze | A61B 17/07207 227/175.2 |
| 5,447,265 A | * | 9/1995 | Vidal | A61B 17/07207 227/176.1 |
| 5,673,842 A | * | 10/1997 | Bittner | A61B 17/07207 227/175.2 |
| 5,728,110 A | * | 3/1998 | Vidal | A61B 17/07207 128/898 |
| 7,617,961 B2 | * | 11/2009 | Viola | A61B 17/07207 227/175.1 |
| 7,658,312 B2 | * | 2/2010 | Vidal | A61B 17/07207 227/175.1 |
| 8,141,762 B2 | * | 3/2012 | Bedi | A61B 17/0644 227/176.1 |
| 8,365,971 B1 | | 2/2013 | Knodel | |
| 8,893,946 B2 | * | 11/2014 | Boudreaux | A61B 17/068 227/175.1 |
| 2011/0101069 A1 | | 5/2011 | Bombard et al. | |
| 2012/0223123 A1 | | 9/2012 | Baxter, III et al. | |
| 2012/0312861 A1 | | 12/2012 | Gurumurthy et al. | |

FOREIGN PATENT DOCUMENTS

| | | |
|---|---|---|
| CN | 201617886 U | 11/2010 |
| CN | 202218889 U | 5/2012 |
| CN | 103037782 A | 4/2013 |
| CN | 103181803 A | 7/2013 |
| CN | 103654900 A | 3/2014 |
| CN | 203634228 U | 6/2014 |
| DE | 3819292 C1 | 7/1989 |
| JP | 29010797 | 8/1954 |
| JP | 2007190622 A | 8/2007 |
| JP | 2010069307 A | 4/2010 |
| WO | 94/24943 A1 | 11/1994 |
| WO | 2013/022708 A1 | 2/2013 |

* cited by examiner

LINEAR CUTTING STAPLER

This application is a U.S. National Phase of International Application No. PCT/CN2014/093677, filed Dec. 12, 2014, which claims priority to China Patent Application Nos. 201310691699.6, filed Dec. 17, 2013 and 201320831894.X, filed Dec. 17, 2013, the disclosures of which are all incorporated herein by reference.

TECHNICAL FIELD

The invention belongs to the technical field of medical apparatus and instruments and particularly relates to a linear cutting stapler.

BACKGROUND

Linear cutting staplers are widely used in surgical operations such as wound closure and the closure and excision of internal tissue. A typical linear cutting stapler as disclosed in U.S. Pat. No. 5,129,570 performs two functions of stapling and cutting, to remove the redundant tissue while stapling the wound. This kind of linear cutting stapler generally includes two jaws (i.e., an upper jaw and a lower jaw), closing handles (i.e., an upper handle and a lower handle) for closing the upper jaw and the lower jaw, an anvil and a staple cartridge arranged opposite to each other at the distal ends of the upper jaw and lower jaw respectively, a staple pushing rod and a cutter which are arranged in the staple cartridge and are moveable synchronously relative to the staple cartridge, and a firing mechanism for driving movement of the staple pushing rod and the cutter. Staples are arranged inside the staple cartridge. The staple pushing rod pushes the staple pushers successively and pushes the staples towards the anvil. At the same time, the cutter cuts off the tissue between the staple cartridge and the anvil.

Before use, the upper and lower jaws are in detached states with each other. While using the stapler, the tissues should be located between the anvil and the cartridge, and then the portion of tissues required operation is fixed by the closure of stapler with the actions of upper and lower closing handles. However, in the practical surgery operation, due to the deviation of setting place of tissue or other reasons, the tissues need to be re-located, which means that the operator should respectively hold the upper jaw and the lower jaw being detached again, which causes inconvenience in operation.

SUMMARY

An object of the invention is to provide linear cutting stapler, which can be lifted up by holding any one of the two jaws and is convenient for use.

For realizing the above-mentioned objectives, the invention provides as linear cutting stapler, comprising an upper jaw and a lower jaw capable of being closed or open relative to each other, said upper jaw includes an anvil and said lower jaw includes a staple cartridge frame; the proximal end of said anvil is provided with a positioning pin, and the proximal end of said staple cartridge frame is configured with a pin slot; or, the proximal end of said staple cartridge frame is provided with a positioning pin, and the proximal end of said anvil is configured with a pin slot; wherein, said pin slot comprises a first slot position and a second slot position which are engaged with said positioning pin, and, said first slot position and said second slot position are partially combined and arranged in an angle with each other; when said upper jaw and said lower jaw rotate from closed state to open state with said positioning pin as a support shaft, said positioning pin actively rotates from said first slot position to said second slot position in which it gets stuck.

As to further aspect, inner wall of said pin slot is provided with an avoiding part between said first slot position to said second slot position; when said upper jaw and said lower jaw rotate from closed state to open state with said positioning pin as a support shaft, said positioning pin actively rotates from said first slot position to said second slot position via said avoiding part.

As a further aspect, while said positioning pin is in said first slot position, said positioning pin abuts against with said first slot position in the axial direction of said stapler; while said positioning pin is in said second slot position, said positioning pin is stuck in said second slot position at least in vertical direction.

As a further aspect, the section of said positioning pin is in waist shape, said positioning pin comprises two waist portions opposite to each other and two arcuate portions respectively connect to said two waist portions.

As a further aspect, said two waist portions are parallel or not parallel with each other, and each said waist portion is straight or curved.

As a further aspect, width of said first slot position in the axial direction of said staple cartridge frame is less than that of said second slot position in the axial direction of said staple cartridge frame.

As a further aspect, when said positioning pin rotates to said second slot position, width of said positioning pin in axial direction of said staple cartridge frame is greater than opening width of said first slot position.

As a further aspect, each of two opposite inner walls of said first slot position include a first stop portion and a second stop portion which are engaged with the waist portion of said positioning pin, said first stop portion and said second stop portion are dislocated in depth direction of said first slot position.

As a further aspect, said second slot position includes a first holding portion and a second holding portion which are arranged concavely on the two opposite inner wall of said first slot position respectively, said first holding portion and said second holding portion are dislocated in depth direction of said first slot position to abut against with the arcuate portion of said positioning pin which rotates to said second slot position.

As a further aspect, distance between said two waist portions of said positioning pin is less than distance between the tops of two arcuate portions.

As a further aspect, said first slot position is perpendicular to axial direction of said lower jaw.

As a further aspect, said positioning pin protrudes two opposite side walls of said anvil, said staple cartridge frame comprises two opposite plate-like portions coupled to each other, said pin slot is formed at the corresponding positions of said two opposite plate-like portions respectively.

As a further aspect, bottom of said second slot position is higher than bottom of said first slot position.

As a further aspect, said pin slot is configured to that when said positioning pin is rotating between said first slot position and said second slot position, rotating center of said positioning pin will not displace in vertical direction and axial direction of said staple cartridge frame.

As a further aspect, while said upper jaw and said lower jaw rotate from open state to closed state with said positioning pin as a support shaft, said positioning pin actively rotates from said second slot position back to said first slot position.

As a further aspect, intersection angle between said first slot position and said second slot position is within 15 degrees~30 degrees.

As a further aspect, the intersection angle between said first slot position and said second slot position is 22 degrees.

Compared with the prior art, the linear cutting stapler provided by the present invention with the technical features that the positioning pin mounted in the anvil and the pin slot configured in the staple cartridge frame, or the positioning pin mounted in the staple cartridge frame and the pin slot configured in the anvil, the pin slot comprising a first slot position and a second slot position which are engaged with the positioning pin, thus, while the upper jaw and the lower jaw are closed, the positioning pin is engaged with the first slot position to locate the upper jaw and the lower jaw related to each other; and while the upper jaw and the lower jaw are open from the closed state, the positioning pin rotates as the support shaft for rotating from the first slot position to the second slot position and gets stuck in the second slot position, by this time the operator can lift up the whole stapler by holding upper or lower jaw, which is convenient for re-locating the tissue and simplifies the operations.

DETAILED DESCRIPTION

Hereinafter, embodiments are described in detail with reference to the accompanying drawings. However, these embodiments can't be used for limiting the scope of present invention, any other equivalent deformations or modifications of structures, methods or functions which are made by the technical persons in the art according to these embodiments are all intended to be included in the scope of invention.

The terms describing places or directions in the description are determined by taking the position of operator as reference, wherein, the "proximal end" is the end close to operator, and the "distal end" is the end far away from operator.

The terms such as "upper", "lower", "first" and "second" in the description are not intended to imply positional relationship or absolutely differentiate the relationship in structure or function. Furthermore, in different embodiments, same labels or reference signs may be used, which doesn't represent certain connections in structure or function, and merely for convenience in describing.

Figure 1:
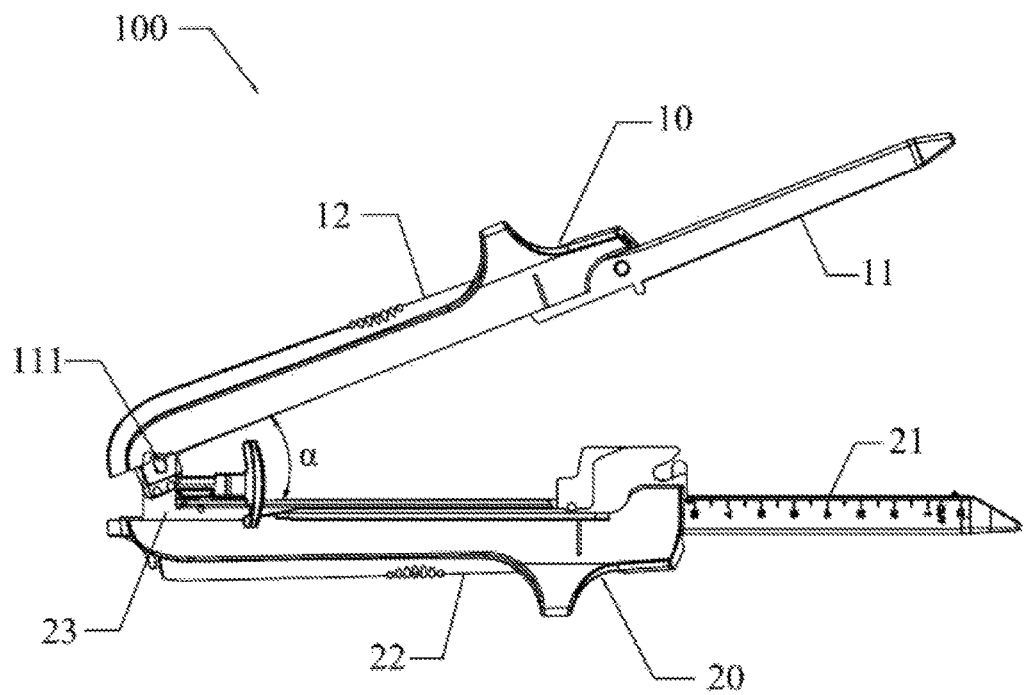
FIG. 1 is a view of a linear cutting stapler with its upper jaw and lower jaw in open state according to an embodiment of the present invention.
Figure 2:
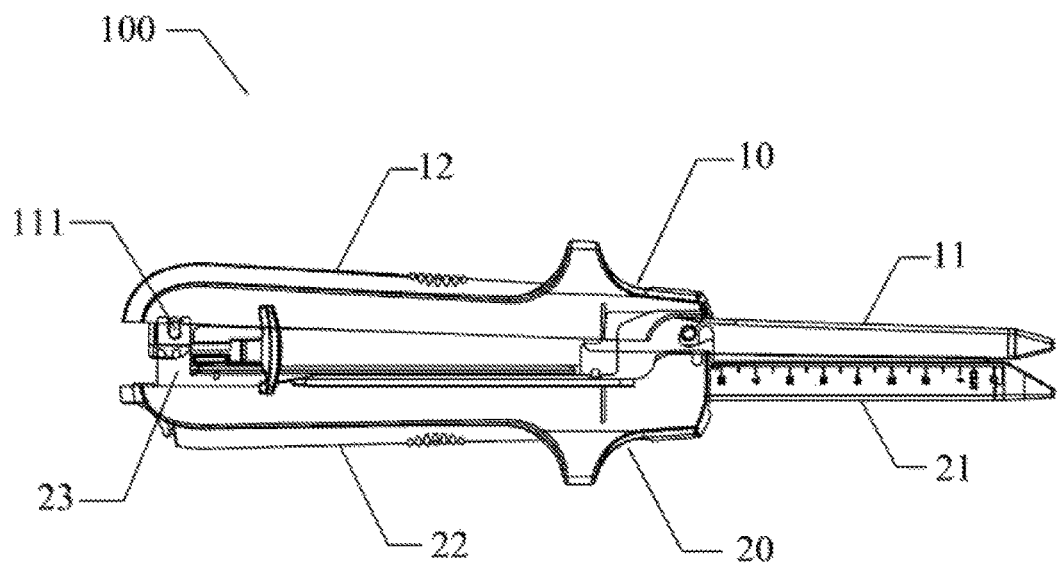
FIG. 2 is a view of a linear cutting stapler with its upper jaw and lower jaw in closed state according to an embodiment of the present invention.
Figure 3:
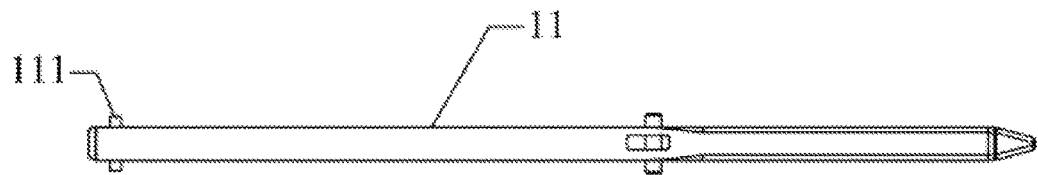
FIG. 3 is a top view of anvil according to an embodiment of the present invention.
Figure 4:
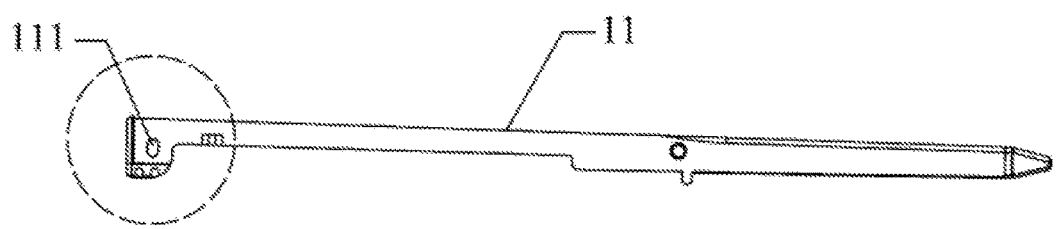
FIG. 4 is a side view of anvil according to an embodiment of the present invention.

Referring to FIG. 1 and FIG. 2, a linear cutting stapler 100 according to one embodiment of present invention is presented. In this embodiment, the linear cutting stapler 100 comprises an upper law 10 and a lower jaw 20 capable of being closed or opened relative to each other. Wherein, the open state and the closed state of two jaws 10, 20 are shown in FIGS. 1 and 2 respectively.

The upper jaw 10 comprises an anvil assembly (with no reference sign) which includes an anvil 11 and an upper handle 12 coupled with the anvil 11. The lower jaw 20 comprises a staple cartridge assembly (with no reference sign) which includes a staple cartridge frame 23, a staple cartridge 21 mounted on the staple cartridge frame 23 and a lower handle 22 coupled with the staple cartridge frame 23. While the upper jaw 10 and the lower jaw 20 are closed, tissues are fixed and clamped between the anvil 11 and the staple cartridge 21 by holding the upper handle 12 and the lower handle 22 so as to cut, suture and other operations. For convenience of describing, in the description, the up and down directions are simplified as vertical direction, and, the extension directions of the upper jaw 10, the lower jaw 20, the anvil 11 and the staple cartridge frame 23 are described as their axial direction respectively, namely, "the axial direction of staple cartridge frame", "the axial direction of stapler", "the axial direction of upper jaw" and "the axial direction of lower jaw".

Referring to FIG. 3 to FIG. 7, the proximal end of the anvil 11 is provided with a positioning pin 111, and the proximal end of the staple cartridge frame 23 is configured with a pin slot 231. The pin slot 231 comprises a first slot position P1 and a second slot position P2 which are engaged with the positioning pin 111. When the upper jaw 10 and the lower jaw 20 are closed, the positioning pin 111 within the anvil 11 is engaged with the first slot position P1 to locate the upper jaw 10 and the lower jaw 20 related to each other.

Figure 5:
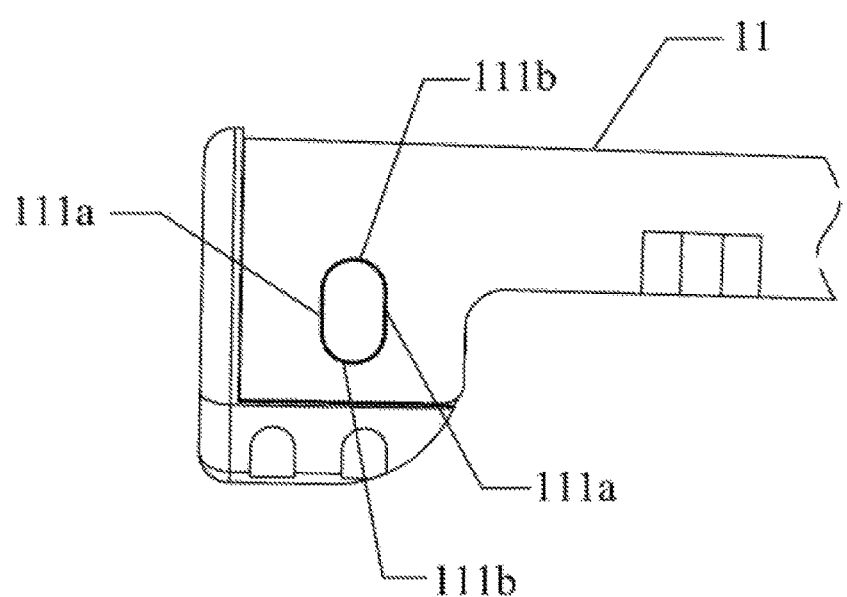
FIG. 5 is an enlarged view of the portion enclosed in imaginary line shown in FIG. 4.
Figure 6:
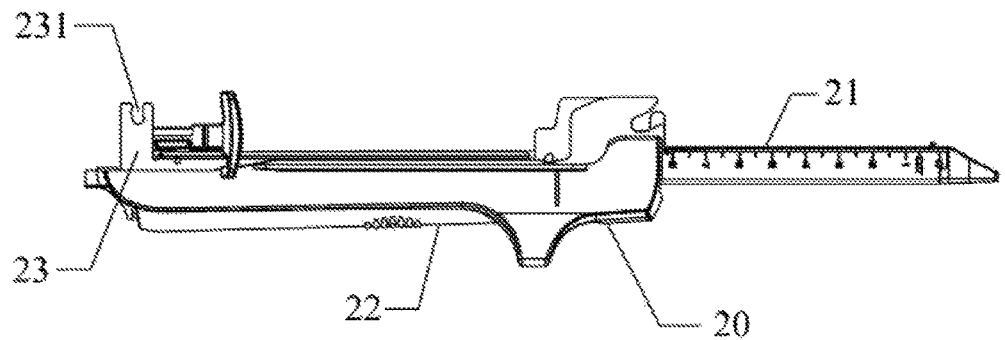
FIG. 6 is a perspective view of the lower jaw according to an embodiment of the present invention.

With reference to FIG. 5, specifically, in this embodiment, the positioning pin 111 inserts vertically into and engages with the first slot position P1 through the upper opening of the first slot position P1. The section of the positioning pin 111 is in waist shape. The positioning pin 111 in waist shape comprises two waist portions 111a opposite to each other and two arcuate portions 111b respectively connect to the two waist portions 111a. In this embodiment, the distance between two waist portions 111a of the positioning pin 111 (namely, the width of waist described hereinafter) is less than the distance between the tops of two arcuate portions 111b. The "waist shape" described in the description is not limited to the pattern shown in FIG. 5, but broadly defined to include the following situations: two waist portions 111a may be parallel or not parallel with each other, and each the waist portion 111a is straight or curved.

Figure 7:
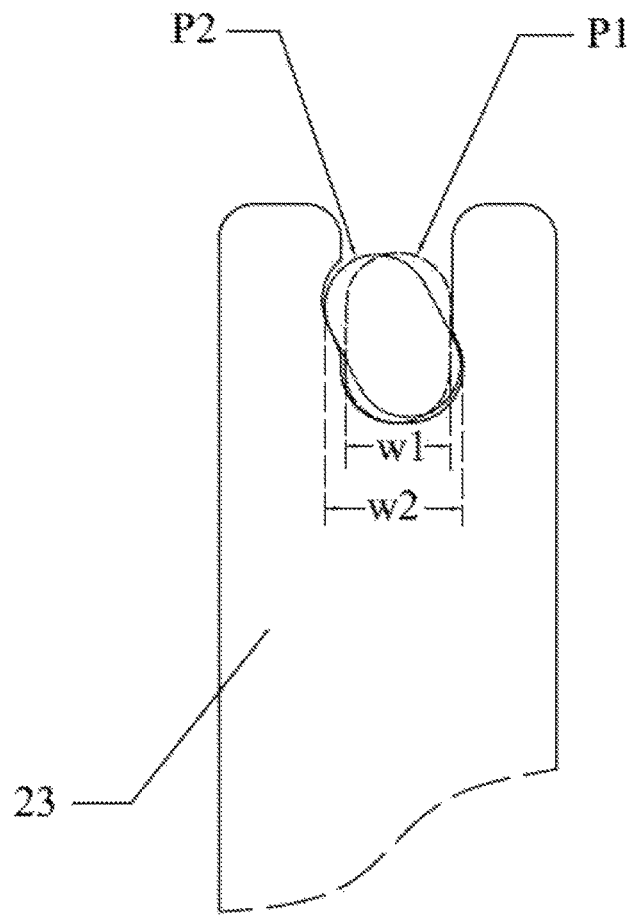
FIG. 7 is a schematic view of the pin slot according to an embodiment of the present invention.
Figure 8:
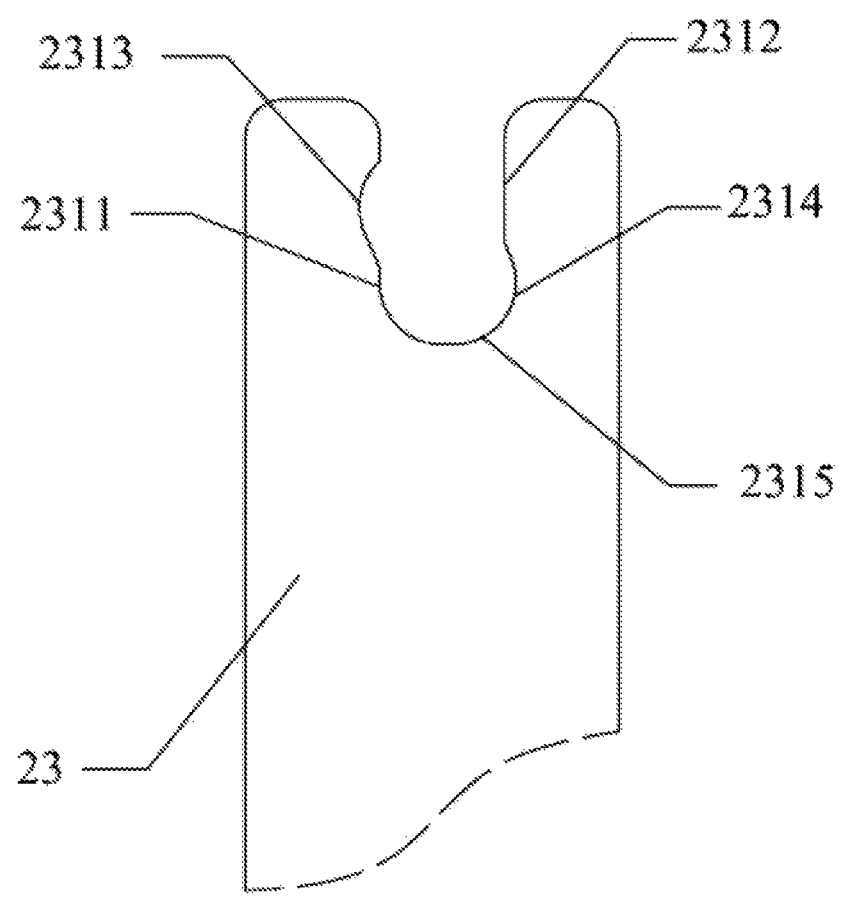
FIG. 8 is a schematic view of the pin slot according to an embodiment of the present invention.

Referring to FIGS. 7 and 8, the two opposite inner walls (with no reference sign) of the first slot position P1 respectively include a first stop portion 2311 and a second stop portion 2312 which are engaged with the waist portion 111a of the positioning pin 111. In the axial direction of the staple cartridge frame 23, the distance between the first stop portion 2311 and the second stop portion 2312 is almost the same with the width of waist of the positioning pin 111 to make the positioning pin 111 abut against with the first slot position P1 thereby restricting the place of the positioning pin 111.

The first slot position P1 and the second slot position P2 are partially combined and arranged in an angle with each other. When the upper jaw 10 and the lower jaw 20 rotate from closed state to open state with the positioning pin 111 as a support shaft, the positioning pin 111 actively rotates from the first slot position P1 to the second slot position P2 in which it gets stuck. While the positioning pin 111 is in the second slot position P2, the positioning pin 111 is stuck in the second slot position P2 at least in vertical direction. When the upper jaw 10 and the lower jaw 20 rotate from open state to closed state with the positioning pin 111 as a support shaft, the positioning pin 111 actively rotates from the second slot position P2 back to the first slot position P1 continuously. With the force of operator, the positioning pin 111 can leave away from the pin slot 231 to realize the separation between the upper jaw 10 and the lower jaw 20.

With reference to FIG. 7, more specifically, the width w1 of the first slot position P1 in the axial direction of the staple cartridge frame 23 is less than the width w2 of the second slot position P2 in the axial direction of the staple cartridge frame 23. The inner wall of the pin slot 231 is provided with an avoiding part 2315 between the first slot position P1 to the second slot position P2. The avoiding part 2315 is configured to allow the positioning pin 111 to actively rotate from the first slot position P1 to the second slot position P2. While the upper jaw 10 and the lower jaw 20 are closed, the positioning pin 111 is engaged with the first slot position P1 of the pin slot 231 for locating. When the upper jaw 10 and the lower jaw 20 rotate from closed state to open state, the positioning pin 111 actively rotates through the avoiding part 2315 and then to the second slot position P2. As the width w2 of the second slot position P2 in the axial direction of the staple cartridge frame 23 is greater than the width w1 of the first slot position P1 in the axial direction of the staple cartridge frame 23, the positioning pin ill can not escape from the pin slot 231.

In operation, if the upper jaw 10 and the lower jaw 20 need to be open to re-locate the tissue between the anvil 11 and the staple cartridge 21, preferably the upper jaw 10 and the lower jaw 20 do not have to separate from each other, and the operator in surgery can use one hand to hold the stapler with open jaws (the upper jaw 10 and the lower jaw 20) and free the other hand for re-locating tissues, which can increase the convenience of operation predictably. The holding effect of the second slot position P2 for the positioning pin 111 can keep the upper jaw 10 and the lower jaw 20 open a certain angle, which allow the operator to lift up the whole linear cutting stapler 100 by holding the upper jaw 10 or the lower jaw 20 with one hand.

In line with the rotational movement of positioning pin 111 in the pin slot 231, the first stop portion 2311 and the second stop portion 2312 are misaligned in the depth direction of the first slot position P1.

Specifically, the second slot position P2 includes a first holding portion 2313 and a second holding portion 2314 which are arranged concavely on the two opposite inner wall of the first slot position P1. While the positioning pin 111 is engaged with the second slot position P2, its two arcuate portions 111b are at least partially engaged in the first holding portion 2313 and the second bolding portion 2314, and at this time, the width of the positioning pin 111 in the axial direction of the staple cartridge frame 23 is greater than the opening width of said first slot position P1, thus the first holding portion 2313 and the second holding portion 2314 block the positioning pin 111 together, which makes the positioning pin 111 can not escape from the second slot position P2 and the first slot position P1 of the pin slot 231.

More preferably, the first holding portion 2313 and the second holding portion 2314 are misaligned in the depth direction of the first slot position P1 and the bottom of the second slot position P2 is higher than the bottom of the first slot position P1. The pin slot is configured to so that when the positioning pin 111 is rotating between the first slot position P1 and the second slot position P2, the rotating center of the positioning pin 111 will not displace.

The intersection angle between the first slot position P1 and the second slot position P2 defines the maximum opening angle α between the upper jaw 10 and the lower jaw 20. Of course, in an alternative embodiment, if the first holding portion 2313 and the second holding portion 2314 are corresponding with each other in the depth of the first slot position P1 (namely, with the same depth), the maximum opening angle between the upper jaw 10 and the lower jaw 20 is defined to 90 degrees.

In one embodiment of the present invention, the intersection angle between the first slot position P1 and the second slot position P2 is within 15 degrees~30 degrees. In a preferred embodiment of the present invention, the intersection angle between the first slot position P1 and the second slot position P2 is 22 degrees. If the intersection angle between the first slot position P1 and the second slot position P2 is too large, the upper jaw 10 and the lower jaw 20 will be easy to detached due to the overlarge opening angle. However, if the opening angle between the upper jaw 10 and the lower jaw 20 is too small, it will go against to clamp tissues.

While the upper jaw 10 and the lower jaw 20 is in the closed state, the positioning pin 111 is perpendicular to the axial direction of the upper jaw 10, and the first slot position P1 is perpendicular to the axial direction of the lower jaw 20, that is, the first slot position P1 and the positioning pin 111 can be engaged for locating the upper jaw 10 and the lower jaw 20 in the axial direction to ensure that the anvil 11 and staple cartridge 21 corresponding to each other. As a variant embodiment, the positioning pin 111 may be inclined relative to the axial direction of upper jaw 10, and the first slot position P1 can also be inclined relative to the axial direction of lower jaw 20, the inclined angle of both are the same. As a further variant embodiment, the positioning pin 111 may even be parallel with the axial direction of upper jaw 10, the first slot position P1 can also be parallel with the axial direction of lower jaw 20, and the second slot position P2 is inclined or perpendicular relative to the axial direction of the lower jaw 20.

In this embodiment, the positioning pin 111 protrudes from the two opposite side walls of the anvil 11, the staple cartridge frame 23 comprises two opposite plate-like portions (with no reference signs) coupled to each other, the pin slot 231 is formed at the corresponding positions of the two opposite plate-like portions respectively, and the portion of positioning pin 111 which protrudes from the two opposite side walls of the anvil 11 is held on the two opposite plate-like portions of the staple cartridge frame 23 where the pin slot 231 is formed. As a variant embodiment, the positioning pin 111 may be integrally formed with the anvil 11, or, in this embodiment, the anvil 11 is provided with a through hole adapted with the positioning pins 111, and the positioning pins 111 is mounted on the anvil 11 via the through hole.

In an alternative embodiment of the present invention, the positioning pins 111 may be arranged at the proximal end of the staple cartridge frame 23 of lower jaw 20, and the pin slot 231 may be formed at the proximal end of the anvil 11 of upper jaw 10. Similarly, it can achieve the effect of lifting up the whole linear cutting stapler with the operator holding, the upper jaw 10 or the lower jaw 20. The other details of this embodiment are the same as that of the embodiments abovementioned, thus no need to repeat herein.

The present invention can achieve the following effects: the linear cutting stapler provided by the embodiments of present invention with the technical features that the positioning pin mounted in the anvil and the pin slot configured in the staple cartridge frame, or the positioning pin mounted in the staple cartridge frame and the pin slot configured in the anvil, the pin slot comprising a first slot position and a second slot position which are engaged with the positioning pin, thus, while the upper jaw and the lower jaw are closed, the positioning pin is engaged with the first slot position to locate the upper jaw and the lower jaw related to each other; and while the upper jaw and the lower jaw are open from the closed state, the positioning pin rotates as the support shaft for rotating from the first slot position to the second slot position and gets stuck in the second slot position, by this time the operator can lift up the whole stapler by holding upper jaw or lower jaw, which is convenient for re-locating the tissue and simplifies the operations. In addition, the positioning pin of the linear cutting stapler provided by the embodiments of present invention is fixed on the frame of anvil without being fall off, which is conferring a good stability for stapler product, also, while the positioning pin is engaged with the pin slot, the upper jaw and the lower jaw can be precisely located in each state of the stapler, which is conferring a strong reliability for the product function.

It should be understood that although the description is presented in accordance with these embodiments, but not every embodiment contains only a single technical solution, only for the sake of clarity. Those skilled in the art should take the description as a whole to combine technical solutions in these embodiments to form the other embodiments which can be understood.

A series of detailed instructions listed above are merely a specific description for the practical embodiments of present invention, which are not intended to limit the scope of the present invention. All the equivalent embodiments or variants without departing away from the spirit of present invention should be included within the scope of the present invention.

What is claimed is:

1. A linear cutting stapler, comprising:
an upper jaw and a lower jaw capable of being closed or open relative to each other, wherein the upper jaw comprises an anvil and the lower jaw comprises a staple cartridge frame and wherein the upper jaw is removably attached to the lower jaw through an engaging unit, wherein:
the engaging unit comprises a positioning pin and a pin slot, wherein the positioning pin and the pin slot are respectively located at a proximal end of the anvil and a proximal end of the staple cartridge frame or respectively located at the proximal end of the staple cartridge frame and the proximal end of the anvil,
the positioning pin is configured to engage the pin slot when the upper jaw and the lower jaw rotate about the positioning pin, such that the positioning pin works as a support shaft when the upper jaw and the lower jaw rotate,
when the linear cutting stapler is in an open state, the positioning pin is in a first slot position of the pin slot and when the linear cutting stapler is in a closed state, the positioning pin is in a second slot position, and
the second slot position is arranged in an angle with respect to the first slot position, such that when the upper jaw and the lower jaw rotate from the closed state to the open state, the positioning pin is held in the second slot position, causing the upper jaw to remain attached to the lower jaw.

2. The linear cutting stapler according to claim 1, wherein:
an inner wall of the pin slot further comprises a retrieving portion located between the first slot position and the second slot position, and
the positioning pin rotates around the retrieving portion of the pin slot, when the upper jaw and the lower jaw rotate about the positioning pin from the closed state to the open state.

3. The linear cutting stapler according to claim 2, wherein:
when the positioning pin is in the first slot position, the positioning pin is aligned with the axial direction of the pin slot, and
when the positioning pin is in the second slot position, at least a vertical movement of the positioning pin is restrained.

4. The linear cutting stapler according to claim 1, wherein a cross-section of the positioning pin comprises two opposing arcuate portions connected by two opposing waist portions.

5. The linear cutting stapler according to claim 4, wherein the two opposing waist portions have straight and parallel edges.

6. The linear cutting stapler according to claim 4, wherein the pin slot further comprises a first stop portion and a second stop portion,
the first stop portion and the second stop portion each engage one of the two opposing waist portions of the positioning pin, and
the first stop portion and the second stop portion are respectively positioned at the two opposing inner walls of the pin slot and in different distances from the bottom of the pin slot.

7. The linear cutting stapler according to claim 4, wherein:
the pin slot further comprises a first holding portion and a second holding portion,
the first holding portion and the second holding portion have a concave shape and are each positioned at one of the two opposing walls of the pin slot and in different distances from the bottom of the pin slot,
the first holding portion and the second holding portion each enage one of the two opposing arcuate portions of the positioning pin, thereby causing the upper jaw to remain attached to the lower jaw when the linear cutting stapler is in the open state.

8. The linear cutting stapler according to claim 4, wherein distance between said two waist portions of said positioning pin is less than distance between the tops of two arcuate portions.

9. The linear cutting stapler according to claim 1, wherein the width of said positioning pin in the axial direction of said staple cartridge frame when said positioning pin is in the first slot position, is less than the width of said positioning pin in the axial direction of said staple cartridge frame when said positioning pin is in the second slot position.

10. The linear cutting stapler according to claim 1, wherein when said positioning pin is in second slot position, the width of said positioning pin in axial direction of said staple cartridge frame is greater than opening width of said pin slot.

11. The linear cutting stapler according to claim 1, wherein; said first slot position is perpendicular to the axial direction of said lower jaw.

12. The linear cutting stapler according to claim 1, wherein: said positioning pin protrudes two opposite side walls of said anvil, said staple cartridge frame comprises two opposite plate-like portions coupled to each other, and said pin slot is formed at the corresponding positions of said two opposite plate-like portions respectively.

13. The linear cutting stapler according to claim 1, wherein: when the positioning pin is in the second slot position, bottom of the positioning pin is higher than the bottom of the positioning pin when the positioning pin is in the first slot position.

14. The linear cutting stapler according to claim 1, wherein when said positioning pin is rotated between said first slot position and said second slot position, the rotating center of said positioning pin remains unchanged in the vertical direction and the axial direction of said staple cartridge frame.

15. The linear cutting stapler according to claim 1, wherein when said upper jaw and said lower jaw rotate from the open state to the closed state with said positioning pin as a support shaft, said positioning pin actively rotates from said second slot position back to said first slot position.

16. The linear cutting stapler according to claim 1, wherein intersection angle between said first slot position and said second slot position is from 15 degrees to 30 degrees.

17. The linear cutting stapler according to claim 16, wherein the intersection angle between said first slot position and said second slot position is 22 degrees.

* * * * *